United States Patent
Stolarczyk et al.

Patent Number: 5,686,841
Date of Patent: *Nov. 11, 1997

[54] APPARATUS AND METHOD FOR THE DETECTION AND MEASUREMENT OF LIQUID WATER AND ICE LAYERS ON THE SURFACES OF SOLID MATERIALS

[75] Inventors: Larry G. Stolarczyk; Gerald Lee Stolarczyk, both of Raton, N. Mex.

[73] Assignee: Stolar, Inc., Raton, N. Mex.

[*] Notice: The term of this patent shall not extend beyond the expiration date of Pat. No. 5,474,261.

[21] Appl. No.: 572,244

[22] Filed: Dec. 13, 1995

Related U.S. Application Data

[62] Division of Ser. No. 982,829, Nov. 30, 1992, abandoned.
[51] Int. Cl.$^6$ .................... G01N 22/00; G01K 27/04
[52] U.S. Cl. .................... 324/635; 324/633; 324/637; 324/648; 244/134 F; 340/582
[58] Field of Search .................... 324/633, 635, 324/637, 644, 647, 648; 343/700 MS; 244/134 R, 134 D, 134 E, 134 F; 340/580, 581, 582

[56] References Cited

U.S. PATENT DOCUMENTS

| | | | |
|---|---|---|---|
| 5,072,172 | 12/1991 | Stolarczyk | 324/332 |
| 5,440,238 | 8/1995 | Martens et al. | 324/644 X |
| 5,474,261 | 12/1995 | Stolarczyk et al. | 244/134 F |
| 5,497,098 | 3/1996 | Heil et al. | 324/647 X |

OTHER PUBLICATIONS

R.N. Grubb, P.L. Orswell, J.H. Taylor, "Borehole measurements of conductivity and dielectric constant in the 300 KHz to 25 MHz frequency range," Radio Science, vol. 11, No. 4, pp. 275–283, Apr. 1976 (Published by the American Geophysical Union, Washington, DC).

*Primary Examiner*—Ernest F. Karlsen
*Assistant Examiner*—Diep Do
*Attorney, Agent, or Firm*—Thomas E. Schatzel; Law Offices of Thomas E. Schatzel a Prof. Corporation

[57] ABSTRACT

An embodiment of the present invention is a roadway sensor for surface installation in a hole such that a thin ceramic contact sensor may be used to measure and cross-compare fundamental physical antenna parameters of the space immediately above a roadway or bridge surface. Measurements are combined by a microprocessor to discriminate between dry pavement, water (rain), snow and ice above the sensor head. Ambient surface temperature, water depth and ice/slush conditions are determined to estimate any hydroplaning hazard and ice/antifreeze/water mixtures. The sensor comprises an antenna that exhibits a resonant frequency and an input admittance including a real term; a Maxwell bridge coupled to the antenna for detecting the resonant frequency, input admittance and real term; and a frequency sweeping oscillator for driving the antenna at a plurality of frequencies proximate in frequency to the resonant frequency. A phase sensitive detector determines an attenuation rate and phase and thereby is able to extract a conductivity ($\sigma$) and a dielectric ($\epsilon$) measurement. The microprocessor relates the conductivity and dielectric measurements to yield, for example, a pair of estimates for ice and water content and layer thickness.

14 Claims, 4 Drawing Sheets

APPARATUS AND METHOD FOR THE DETECTION AND MEASUREMENT OF LIQUID WATER AND ICE LAYERS ON THE SURFACES OF SOLID MATERIALS

This is a divisional of application(s) Ser. No. 07/982,829 filed on Nov. 30, 1992, now abandoned.

BACKGROUND OF THE INVENTION

1. Field of the Invention

The invention relates generally to transportation safety equipment and instruments and specifically to devices capable of detecting and measuring liquid water and/or ice accumulation layer, such as can occur on the surfaces of roadways, bridges, airplane wings and space craft prior to launch. The invention further specifically relates to instrumentation that can determine the effects of varying moisture and electrical parameters on the remote sensor measurement of an in situ layer of coal.

2. Description of the Prior Art

Ice build-up on low temperature fuel tanks, airfoil surfaces and highways can unexpectedly occur and create hazardous conditions for transportation.

Ice build-up on low temperature fuel tanks is a safety concern in NASA's Space Shuttle program. After filling insulated fuel tanks on a booster rocket, the countdown time period is allowed to continue unless any ice build-up is 0.25 inches thick or more. Presently, ice depth measurements are manually made by workers scratching away the ice layer and determining the ice layer thickness. On large upright vehicles, such as the Space Shuttle, the number of such measurements is limited by practical access problems.

Commercial airline disasters in Washington D.C., Denver, Colo., Newfoundland, and recently in Europe, have been suspected to have been caused by ice and snow build-up on the wings of the aircraft. In a preventative attempt to alleviate the potential dangers of ice and snow, air maintenance crews universally spray air foil surfaces with a deicing and anti-icing liquid, e.g., ethylene-glycol, sometimes regardless of whether ice is actually present. In bad weather operating conditions, takeoffs of planes are often delayed because the weather reduces the number of planes that can takeoff and land, which only exacerbates the icing problem because more time is available for the ice to build-up on wings to dangerous thicknesses. This reduces the hold time of the aircraft before takeoff. Hot ethylene-glycol fluid may be sprayed on airfoil surfaces for deicing purposes. Anti-icing ethylene-glycol fluids are sprayed on airfoil surfaces to create a layer for clearing off a wing during takeoff. As snow or rain continues to accumulate, the freezing-point temperature of the anti-freeze mixture increases. During a taxi and hold period, the effectiveness of the anti-icing fluid is compromised. A pilot's vision of his aircraft's surfaces is usually very limited. Pilots waiting to takeoff need a reliable sensor technology that can determine if critical airfoil surfaces have been compromised. Any ice thickness, snow thickness, and slush-ethylene glycol mixture thickness are all important data a pilot would want to have reported. The freezing point of the anti-icing layer must be known.

General aviation operating in icing conditions typically employ deicing technology to remove dangerous ice formations from air foil surfaces. Ice has a tendency to form on the leading edges and other protruding surfaces of an aircraft's superstructure during flight. Through the years, deicing technology has been developed that includes pneumatic bladders, heating elements, and ultrasonic transducers. Such technology requires in-flight fuel during operation. A sensor that automatically starts deicing would save hundreds of millions of dollars in fuel cost.

Roads are also notorious for icing and causing car accidents. The most hazardous ice formations are those that are hard to see, unexpected or irregular. For example, so-called "black ice" will form on bridges long before conditions will freeze ice on the approaches to a bridge. Safety in the nation's highway system depends upon roadway surfaces and vehicle tires maintaining good friction. Water puddles can also make tires come loose of the roadway. Such water causes spinning tires to hydroplane such that the vehicle looses its ability to turn or brake without warning. Black ice and hydroplaning on roadway surfaces and bridges is a leading cause of highway accidents. Highway safety would improve if sensors were used to detect black ice and hydroplaning conditions and ice build-up on bridges. Roadway warning signs could then be automatically illuminated and deicing technology initiated, such as heating coils in the roadway surfaces or other technology to improve driving conditions.

A layer of material to be measured may include a natural media such as coal. Cutting processes for coal layers can be improved if measurement is available. Some coal layers contain various moisture amounts and such variability can impact thickness measurements based on conductivity. Experimental determination of the measurement parameters versus thickness is therefore required.

Many prior art technologies have been investigated and dismissed as being unreliable in their ability to measure ice build-up under adverse weather conditions. One of the technical problems relates to the discrimination of ice, snow, and water conditions on the surface. Another relates to the measurement of the freezing-point of an anti-freeze mixture. Measurement of the overlying material thickness is another problem. The measurement depends on the electrical parameters of the particular layer. Since moisture can change in some coal seams, a method of measuring the electrical parameters of the layer is needed. The same technology is needed to determine the freezing-point of an anti-freeze mixture. Sensor wear is yet another problem. For example, sensors that protrude may unreliably determine ice conditions on airfoil surfaces. A flush sensor that can be conformably mounted is needed. Such a sensor must also be compatible with the thermodynamic properties of surrounding surfaces that are to be monitored by the sensor.

Theoretical and experimental studies of microstrip antennas have shown that an antenna's terminal admittance can be made to be dependent on the depth and dielectric constant and electrical conductivity of an ice, snow, water, water-ethylene glycol or coal layer overlying the antenna. For background art, see U.S. Pat. No. 5,072,172, issued Dec. 10, 1991, to two of the present inventors, Larry G. Stolarczyk and Gerald L. Stolarczyk, and especially the discussion relating to FIG. 10, an airplane wing cross-section. Microstrip antennas are typically constructed by forming conductive layers on a substrate with a relative dielectric constant ($\epsilon_r$) greater than 2.2. The requisite physical size of an antenna will decrease with increases in the dielectric constant. Typical values of relative dielectric constant vary from 2.2 for DUROID™, to approximately 9.8 for TMM-10™ substrate material, which has a lower temperature coefficient. Higher dielectric constant substrates are also technically possible. A microstrip patch may be circular, rectangular or spiral in form. The spiral type may be considered to be a narrow rectangular line with radiation occurring along the edges of a microstrip line. The spiral form may be more sensitive to ice thickness.

Theoretical and experimental investigation of resonant microstrip antenna sensors by the present inventors indicates that a percentage change in a resonant frequency and a conductance due to overlying ice, water or coal layer depth can be detected and measured with a practical instrument. A thin microstrip antenna sensor and computer codes were developed to determine the resonant frequency change of the microstrip antenna due various ice buildups. The result was a more-or-less linear change in resonant frequency from 2500 MHz decreasing to 2150 MHz for ice thicknesses increasing from 0.01 inches to 0.22 inches. The resonant frequency changed by 140 MHz, or 5.6 percent, for each 0.1 inch change in ice layer depth. A 0.25 inch layer of ice caused the resonant frequency of the antenna to decrease by fourteen percent.

To investigate the ice and ice-water layering behavior in more detail, a series of experimental tests were conducted in a temperature-controlled chamber. In these tests, 0.1 inch depth increments of water were added to a tray in which a microstrip antenna sensor was positioned in the bottom of the tray. Resonant frequency and conductance were independently measured after each incremental change in water depth. The measurements were repeated after one hour to allow the 0.1 inch water layer to turn to ice. The test data is listed in Table I.

TABLE I

| DEPTH | ICE | | 0.1" WATER AND ICE | |
|---|---|---|---|---|
| INCHES | $f_o$(MHz) | G(mS) | $f_o$(MHz) | G(mS) |
| 0.0 | 821.21 | 13.4 | 797.09 | 21.5 |
| 0.1 | 812.98 | 15.4 | 784.14 | 28.0 |
| 0.2 | 815.28 | 17.0 | 786.31 | 30.7 |
| 0.3 | 812.07 | 17.7 | 782.00 | 39.4 |
| 0.4 | 805.02 | 22.3 | 772.78 | 55.4 |
| change | 16.9 | 8.9 | 24.31 | 33.9 |
| percent | 1.9 | 66 | 3.05 | 157 |

The resonant frequency changes by 1.9 percent when the ice build-up increases from zero to 0.4 inch. The tests were conducted on an antenna designed for an 821 MHz nominal operating frequency. The resonant conductance changed by sixty-six percent. When the experimental results are compared to theoretical results, a fourteen percent change is expected for an antenna designed to operate at approximately 2400 MHz. The percentage change in resonant frequency is related to the ice thickness and wavelength of the radio signal. At high frequency, the ice thickness spans a greater percentage of the wavelength of the radio wave travel through space. Therefore, the resonant frequency change due to ice layer depth increases with the resonant frequency of the antenna. The physical size of a microstrip antenna may be decreased with increases in resonant frequency. Ice thickness sensitivity and physical size considerations suggest the use of a sensor in the 2000 MHz frequency range.

Experimental test data shows that the resonant frequency change by twenty-four MHz (2.9 percent) when 0.1 inch of water layer covers the antenna. The resonant conductance increases by sixty percent. A sensor can readily detect the presence of water, with a dielectric constant of eighty, instead of ice, with a dielectric constant of four. Anti-freeze mixtures of water and glycerol exhibit a dielectric constant that has been observed to range between twenty-four and eighty. Therefore, water-ethylene-glycol mixtures can be detected with such a microstrip sensor.

Theoretical and experimental investigations further suggest that ice depth can be measured with a resonant microstrip patch antenna. The theoretical results from the published literature and experimental tests show that a protective layer, e.g., a one-eighth inch plastic layer, will decrease the sensitivity of a microstrip patch antenna. In a practical design of a sensor, the protective layer is therefore preferably as thin as is possible. Computer modeling shows that a six percent change in resonant frequency can be expected for each 0.1 inch of ice build-up on the antenna. Experimental data shows that the resonant frequency changes by 2.1 percent and resonant conductance changes by more than thirty-four percent only a 0.1 inch water layer covers an ice layer, the resonant frequency can be expected to decrease by 160 MHz (19.4 percent). The resonant conductance can be expected to increase by 188 percent, which is well within the measuring capability of practical instrumentation. Such instrument design requires that both the resonant frequency and resonant conductance of the antenna be measured to determine ice thickness, as well as to determine if a water layer is present. Where anti-freeze is present in the layer, or where a layer with moisture is to be measured, the resonant frequency will decrease and the resonant impedance will change substantially.

SUMMARY OF THE PRESENT INVENTION

It is therefore an object of the present invention to provide a monitoring system for measuring the presence and thickness of ice on a surface exposed to the weather.

It is a further object of the present invention to provide a means for measuring the freezing point of a water-glycol mixture on an airfoil surface.

It is a further object of the present invention to provide a system for measuring the thickness of a coal layer with varying amounts of moisture.

It is a further object of the present invention to provide an automatic means for warning drivers of the hazards from weather conditions existing on a roadway or bridge.

It is a further object of the present invention to provide an automatic means for warning pilots in the cockpit or via the control tower of the hazards from icing conditions existing on an airplane's airfoils.

It is a further object of the present invention to provide an automatic means for warning mission control personnel of the hazards from ice accumulations existing on a spacecraft liquid oxygen tank.

Briefly, an embodiment of the present invention is a roadway sensor for flush surface installation in a two inch diameter hole such that a thin ceramic contact sensor may be used to measure and cross-compare fundamental physical antenna parameters of the space immediately above a roadway or bridge surface. Measurements are combined by a microprocessor to discriminate between dry pavement, water (rain), snow and ice above the sensor head. Ambient surface temperature, water depth and ice/slush conditions are determined to estimate any hydroplaning hazard and ice/antifreeze/water mixtures. The sensor comprises an antenna that exhibits a resonant frequency and an input admittance including a real term. The measurement can determine the effect that moisture has on the coal layer thickness measurement. A Maxwell bridge is coupled to the antenna for detecting the resonant frequency, input admittance and real term; and a frequency sweeping oscillator for driving the antenna at a plurality of frequencies proximate in frequency to the resonant frequency. A phase sensitive detector determines the resonant frequency and impedance of the sensor microstrip antenna. A second pair of antennas is used to determine the attenuation rate and phase and is thereby able to extract a conductivity (σ) and a dielectric (ε) of the layer measurement. The microprocessor relates the conductivity and dielectric measurements to yield, for example, a pair of estimates for ice and water content and layer thickness.

An advantage of the present invention is that a system is provided that can detect and measure ice and water accumulation layer on a surface exposed to the weather.

Another advantage of the present invention is that a system is provided that can improve highway safety by warning drivers of actual icing or hydroplaning conditions at specific places in a roadway or bridge.

Another advantage of the present invention is that a system is provided that can indicate exactly when and where de-icing and anti-icing procedures are required for an airplane's wings.

A still further advantage of the present invention is that a system is provided that can measure coal layer thickness when the electrical parameters of the layer vary.

These and other objects and advantages of the present invention will no doubt become obvious to those of ordinary skill in the art after having read the following detailed description of the preferred embodiment that is illustrated in the various drawing figures.

DETAILED DESCRIPTION OF THE PREFERRED EMBODIMENTS

Figure 1:
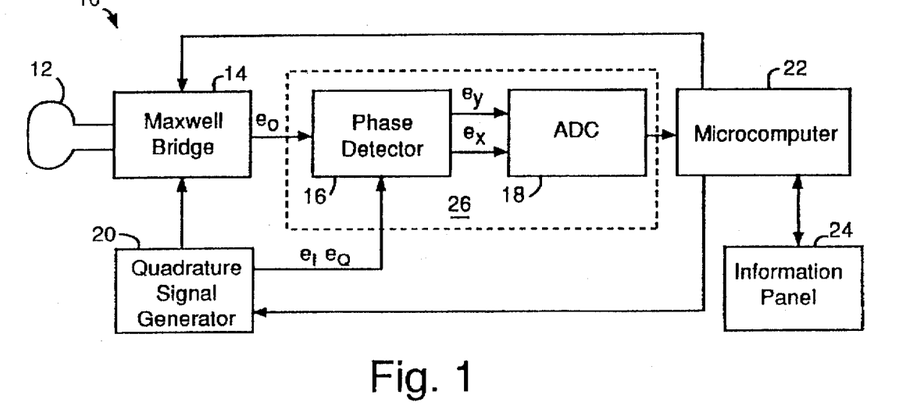
FIG. 1 is a block diagram of a first instrument embodiment of the present invention for detecting and measuring ice and water accumulations.

FIG. 1 illustrates an ice layer thickness measurement instrument embodiment of the present invention, referred to herein by the general reference numeral 10. Instrument 10 comprises a patch antenna 12, a Maxwell bridge 14, a phase detector 16, an analog-to-digital converter (ADC) 18, a quadrature signal generator (QSG) 20, a microcomputer system 22 and a display 24. Antenna 12 is a circular patch antenna with an offset coaxial feedpoint and presents an admittance input term $Y_{in}$. Microcomputer 22 provides a calibration signal to bridge 14 and a frequency control signal to generator 20. Bridge 14 receives a variable frequency drive signal from QSG 20. Instrument 10 measures a resonant frequency ($f_r$) and an input admittance value of microstrip antenna 12. The input admittance (Y) is, $$Y = G + iB, \quad (1)$$

where,

G=input conductance of the antenna in Siemens and

B=input susceptance.

At a resonant frequency ($f_r$), the input susceptance (B) will equal zero.

Antenna admittance measurements are made with a Maxwell bridge configuration, embodied in bridge 14. A bridge output signal ($e_o$) is applied to a phase sensitive detector (PSD) network 26, comprised of phase detector 16 and ADC 18, and is measured by the combination of ADC 18 and microprocessor 22. A control program included in microcomputer 22 computes the admittance, using a pair of measured values for signals $e_x$ and $e_y$ that are acquired via ADC 18. Microprocessor 22 also controls the operating frequency of QSG 20 to determine a resonant frequency ($f_r$) for antenna 12. This is done by incrementing the output frequency ($f_o$) of QSG 20 until the measured input susceptance (B) approaches zero.

Such bridge measurements necessitate that a calibration means be included within antenna 12. The antenna connections are such that an open, a short and fifty ohm resistance may be created to gauge the calibration.

After a measurement of the frequency and conductance at resonance has been completed, data including an identification number for the particular instrument 10 is used to frequency modulate the output signal of QSG 20. Patch antenna 12 will operate to transmit the data to a remote monitoring receiver, e.g., whenever icing is detected. Multiple measuring instruments 10 may be attached to a surface to be monitored for ice formation.

Figure 2:
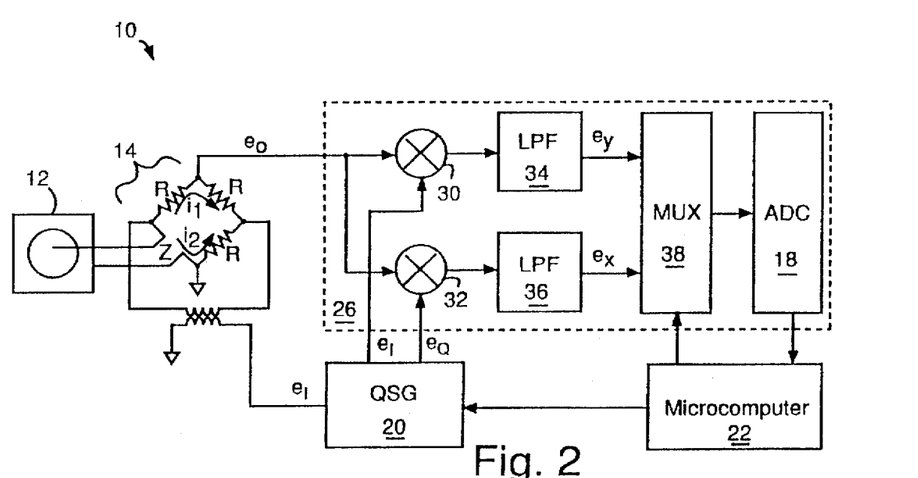
FIG. 2 is a schematic diagram that provides additional detail of selected elements of the instrument of FIG. 1.

FIG. 2 illustrates bridge 14 and PSD 26 in more detail. The input impedance of microstrip antenna 12 is measured with Maxwell bridge 14, PSD 26 and QSG 20. The mathematical functions of each need to be known. Equations for bridge 14 are derived from the network current loop equations as, $$i_1 = \frac{e}{R+R}, \quad (2)$$

$$i_2 = \frac{e}{R+Z}, \quad (3)$$

where

Z is the input impedance of the antenna,

R is the bridge resistance value in ohms, and, $e = E \sin(2\pi f_r t + \theta_1)$ is the bridge source voltage, where E is the peak value of the source voltage, $f_r$ is the operating frequency in Hertz of QSG 20, and $\theta_1$ is the phase of the QSG signal.

The bridge network output voltage ($e_o$) is, $$e_o = (i_2 - i_1) R. \quad (4)$$

Substituting equations (2) and (3) into equation (4) results in the bridge voltage ratio Γ being defined in terms of the bridge impedances, $$\Gamma = \frac{e_o}{e} = \frac{R}{R+Z} - \frac{R}{R+R}. \quad (5)$$

The ratio is a complex number that can be represented by, $$\Gamma = |\Gamma| e^{-i\theta_M}, \quad (6)$$

where

|Γ| is the magnitude-of the ratio, and $\theta_M$ is the measured phase shift.

The antenna input impedance can be computed from, $$Z = \left[ \frac{\frac{1}{2} - \Gamma}{\frac{1}{2} + \Gamma} \right] R. \quad (7)$$

To maximize the change in bridge voltage ratio Γ with a change in Z, it can be shown that the bridge R value should be set equal to real value of Z at resonant frequency of antenna 12.

The measurement of the bridge voltage ratio ($\Gamma = e_o/e$) requires that the magnitude and phase of the bridge source voltage (e) be known, thus calibration is needed. By shorting the two terminals of antenna 12, an inspection of the bridge network shows that the measured output voltage ($e_o$) is, $$e_o = \frac{1}{2} e. \quad (8)$$

By opening the two terminals of antenna 12, the bridge network output voltage becomes, $$e_o = -\frac{1}{2} e. \quad (9)$$

The open circuit condition produces an output voltage that is 180 degrees out of phase with the short circuit condition. In either case, the magnitude of the calibrated bridge output voltage will be one-half of QSG 20 source voltage (e). The magnitude of the quadrature signal is, $$E = 2e_o. \quad (10)$$

Phase calibration of instrument 10 can be established from the open and short-circuit phase data (180°). However, this data is not needed if a synchronous detector is used for the phase sensitive detector network.

The bridge output signal may be represented by, $$e_o = \frac{1}{2} |\Gamma| E \, \text{SIN}(2\pi f_1 t + \theta_1 + \theta_M). \quad (11)$$

FIG. 2 illustrates that PSD 26 comprises a pair of mixers 30 and 32 which respectively mix in-phase injection signal $e_I$ and quadrature-phase injection signal $e_Q$ with output voltage $e_o$ from bridge 14, expressed as, $$e_o \times e_I, \quad (12)$$

$$e_o \times e_Q. \quad (13)$$

A pair of lowpass filters 34 and 36 respectively produce voltages $e_x$ and $e_y$. A multiplexer 38 is controlled by microcomputer 22 to select an input signal for ADC 18. QSG 20 output sinusoids are represented by:

$$e_I = E \, \text{SIN}(\omega t + \theta_1), \quad (14)$$

and $$e_Q = E \, \text{SIN}(\omega t + \theta_1 + 90°). \quad (15)$$

Lowpass filtering of the mixer output signals results in the elimination of all frequency dependent terms, except the DC terms as in:

$$e_x = \frac{1}{2} |\Gamma| E^2 \, \text{SIN}(\theta_M + \theta_1 - \theta_1), \quad (16)$$

and $$e_y = \frac{1}{2} |\Gamma| E^2 \, \text{COS}(\theta_M + \theta_1 - \theta_1). \quad (17)$$

Equations (16) and (17) show that the QSG phase ($\theta_1$) jitter and drift are canceled in mixers 30 and 32. The lowpass filtered PSD mixer output signals can be represented by a phasor diagram, in which the phase of the signals is given by $$\theta_M = \text{TAN}^{-1} e_x/e_y, \quad (18)$$

and the magnitude, $$\frac{1}{2} |\Gamma| = \frac{\sqrt{e_x^2 + e_y^2}}{E^2}. \quad (19)$$

The magnitude of the bridge voltage ratio is, $$|\Gamma| = \frac{2\sqrt{e_x^2 + e_y^2}}{E^2}. \quad (20)$$

The magnitude of the bridge voltage ratio is determined by the ADC 18 measurement of $e_x$ and $e_y$. The value of E is determined during calibration of instrument 10. The microcomputer 22 includes program routines to compute $\theta_M$, Γ, and Z.

With reference to QSG 20, the admittance of patch antenna 12 is measured throughout the frequency band ($BW_M$) of resonant frequencies associated with the range of ice and ice-water depths. The measurement band of frequencies may exceed 160 MHz. The frequency of QSG 20 is automatically swept up and/or down by control signals from microprocessor 22 until the resonant frequency of patch antenna 12 is detected. At resonant frequency, the imaginary part of the antenna input admittance (susceptance) exhibits a value of zero. Quadrature radio frequency signals are applied to the bridge 14 and PSD 26 networks. Microprocessor 22 computes the admittance from the measured values of $e_x$ and $e_y$.

The search for the resonant frequency of antenna 12 may initially start with the output frequency of QSD 20 at a lowest frequency in a predetermined measurement band. The admittance of antenna 12 is measured at this lowest frequency. The output frequency is then incrementally increased, and the admittance measured, until the antenna input susceptance demonstrates a minimum value. At least ten different points within the bandwidth of microstrip antenna 12 are preferably used for each of the incremental output frequency changes. Since the three decibel (dB) bandwidth points of antenna 12 will be separated by approximately three percent of the resonant frequency, an increment frequency changes are preferably smaller than 0.003 of the operating frequency, e.g., 2.4 MHz or smaller increments at 800 MHz resonant frequency. Higher frequency resolution than this is not strictly required in instrument 10.

The in-phase ($e_I$) and quadrature ($e_Q$) radio frequency signals are generated in QSD 20 network, which is essentially a frequency synthesizer with digital control originating in a frequency search program included in microprocessor 22.

Figure 3:
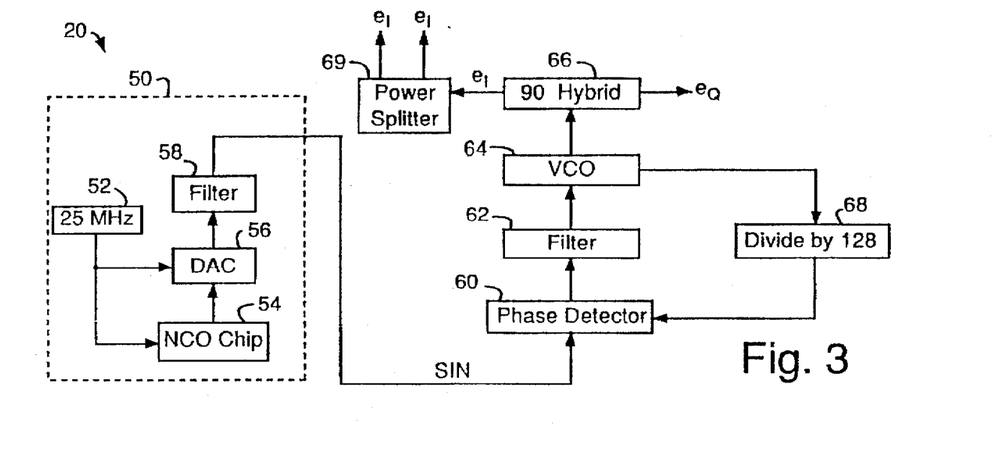
FIG. 3 is a block diagram of the quadrature signal generator included in the instrument of FIGS. 1 and 2.

QSG 20 is illustrated In further detail In FIG. 3. A numerically controlled oscillator (NCO) 50 includes a twenty-five MHz oscillator 52, an integrated circuit (IC)

device 54, an eight-bit digital-to-analog converter (DAC) 56 and an anti-aliasing filter 58. NCO 50 produces a signal output (SIN) that is applied to one input of a phase detector 60. A filter 62 passes the output of phase detector 60 to control a voltage-controlled oscillator (VCO) 64. A 90° hybrid 66 generates the two quadrature signals, $e_I$ and $e_Q$, which are preferably synthesized within a common measurement band. A divide-by-128 counter 68 returns a sample of the output of VCO 64 for phase-locking. A power splitter 69 provides two copies of signal $e_f$. VCO 64 operates in a measurement band that extends from 600 MHz to 1200 MHz. VCO 64 may comprise a Vari-L VCO-120 integrated circuit, which is commercially available. The VCO output signal may alternatively be applied to a power splitter which provides radio frequency input signals to 90° hybrid 66 and the divide-by-128 counter 68. The 90° hybrid 66 generates the quadrature radio frequency signals required in the direct conversion process, and may be comprised of an Adams-Russel 90° hybrid model JH-140 which provides quadrature signals within a band of 500 MHz to 1000 MHz, and with an insertion loss of less than 0.3 dB. The quadrature deviation of such a unit is less than two degrees across the frequency band.

In operation, phase detector 60 and filter 62 force the frequency and phase of the NCO signal (SIN) and the VCO divide-by-128 signal to be identical. The divide-by-128 signal frequency typically extends from 4.6875 MHz to 9.3750 MHz. If the upper tuning band frequency is restricted to 1000 MHz by 90° hybrid 66, then the upper divide-by-128 signal frequency limit will be approximately 7.8125 MHz.

Device 54 is preferably a Stanford Telecom numerically-controlled oscillator product number STEL-1179, which is a CMOS device provided in a 26-pin plastic leaded chip carrier (PLCC) and that can be tuned with a 24-bit serial interface with microprocessor 22. Device 54 provides the granularity of digital tunability required in the frequency synthesis process. With a twenty-five MHz clock, the incremental frequency tuning step is 1.5 Hz. The incremental tuning ability of the frequency synthesizer as a whole is 192 Hz (128×1.5). A Vectron CO-442 ACMOS CMOS clock oscillator may be used for oscillator 52. Anti-aliasing filter 58 can be realized with a Mini Circuits low pass filter.

The $e_I$ and $e_Q$ radio frequency signals may be applied to bridge 14 and PSD 26 in either a direct-conversion frequency transposition processes, as illustrated in FIG. 2, or dual-conversion frequency transposition processes. The direct conversion design has the advantage of circuit simplicity.

Figure 4:
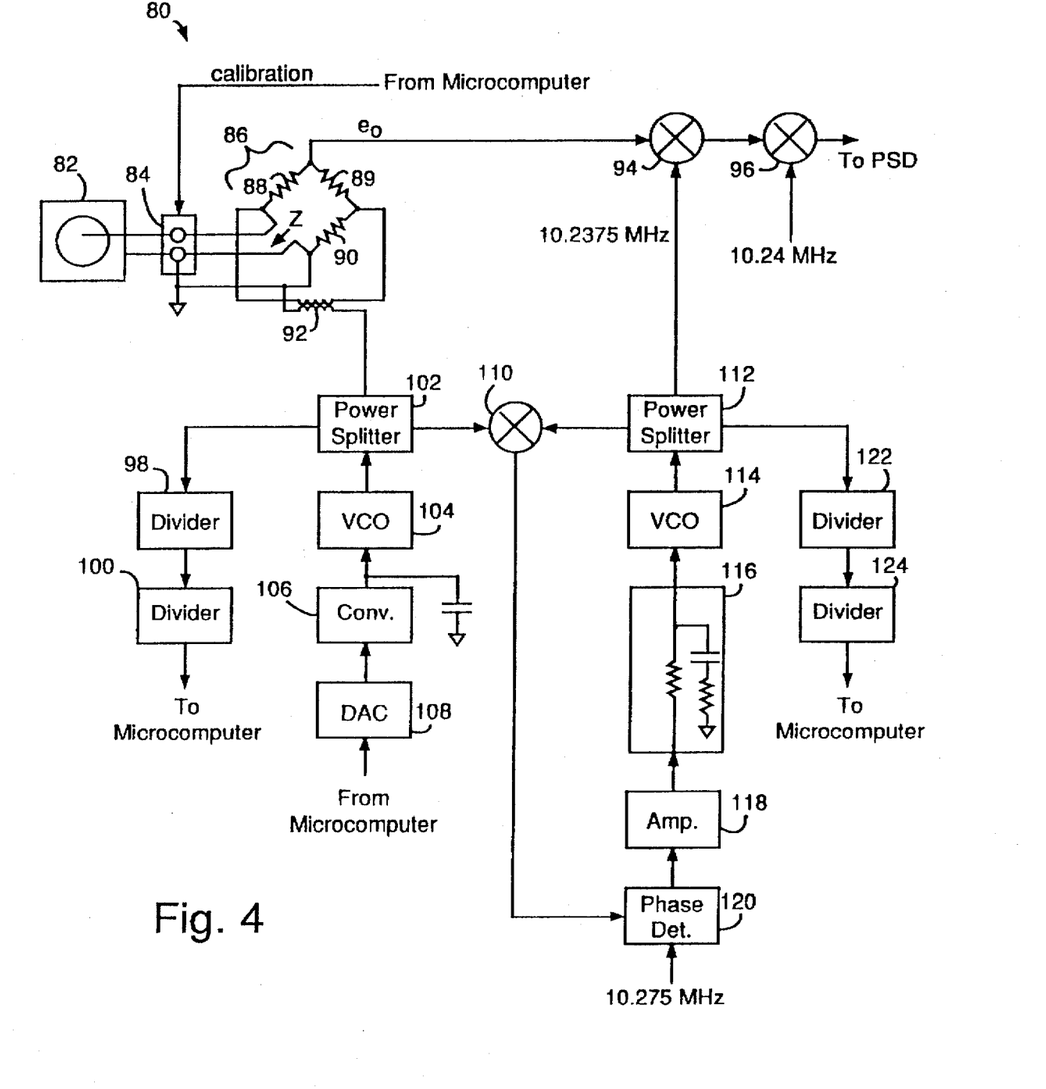
FIG. 4 is a combination schematic and block diagram of a portion of a dual-conversion second instrument embodiment of the present invention, and is otherwise similar to that of FIGS. 1 and 2.

An exemplary dual-conversion scheme is illustrated in FIG. 4. A second instrument embodiment of the present invention, referred to herein by the general reference numeral 80, comprises an antenna 82, an antenna switch 84, a bridge 86 including a set of three resistors 88-90 and a transformer 92, a first IF mixer 94, a second IF mixer 96, a first divider 98, a second divider 100, a first power splitter 102, a first VCO 104, a voltage converter 106, a DAC 108, a PLL mixer 110, a second power splitter 112, a second VCO 114, a filter 116, an amplifier 118, a phase detector 120, a third divider 122 and a fourth divider 124. Mixer 94 accepts a local oscillator (LO) frequency of 10.2375 MHz and mixer 96 uses a LO frequency of 10.24 MHz. An IF frequency of 2.5 KHz is the result and is forwarded to the phase sensitive detector.

In the context of FIG. 1, such a dual-conversion scheme necessitates that another intermediate frequency (IF) stage be positioned between the output port of the bridge and the phase sensitive detector. The dual-conversion scheme is such that the $e_I$ and $e_Q$ signals are generated at only the second IF frequency. The radio frequency signal applied to bridge 14 and first IF mixer are synthesized in the measurement frequency band to produce a constant first IF signal frequency.

The direct and dual-conversion schemes thus employ mixers, filters, and other radio signal processing components to achieve up-frequency conversion. Mixers serve to transpose frequency bands, while doublers and phase locked loops can be used to multiply the frequency (phase) of lower-frequency signals. All the radio frequency signals originate from a common crystal controlled clock so that a phase coherent frequency transposition process can be realized. Frequency tunability comprises digital programming of the frequency of signals.

Alternative configurations of the direct conversion scheme may use frequency doublers and mixers to synthesize the measurement band signals. Up-converter circuits using large integer multiplication of the NCO output signal yield conversion losses of more than eighteen dB. Although the frequency resolution would be degraded by the multiplication factor involved, the resolution would nevertheless be within the frequency step tuning requirements of instrument 10. Mixing of the NCO output signal with 600 MHz crystal oscillator may also be considered, which thereby reduces the multiplication factor. A doubler following the mixer may be used to achieve the appropriate band frequencies. Such circuit schemes require narrow bandpass filters to suppress unwanted frequency components. Mixer frequency transposition further requires suppression of the image band mixer injection signals. Unwanted signal rejection requirements can be relaxed when an NCO output signal is multiplied prior to mixing. Bandpass filtering of the NCO alias band might also be used. However, the amplitude would change in the NCO synthesized output signal band. Up-conversion schemes using only low pass filters require multiple mixers in the frequency transposition process.

In the dual-conversion process illustrated in FIG. 4, VCO 104 is controlled by a DC tuning voltage generated by DAC 108. A digital tuning code is generated by a microprocessor and serially communicated to DAC 108. VCO 104 is part of a mix-down type PLL. The PLL produces an output frequency that is always 10.2375 MHz away from the measurement frequency of VCO 104. A first IF signal frequency is always 10.2375 MHz. The first IF signal is within a gain constant of the output signal of bridge 86. The first IF output signal is mixed with a 10.24 MHz signal in the second mixer 96. A second IF signal at 2500 Hz is applied to the phase sensitive detector. The 10.2375 and 10.24 MHz signals are generated by a coherent frequency source (CFS) circuit, which also generates quadrature signals for the PSD mixers, e.g., mixers 30 and 32.

Microprocessor 22 (FIG. 1) includes a program that computes the admittance of the antenna, generates incremental tuning signals for QSD 20, and performs a modulation function for transmitting data to a remote receiver. The microprocessor may comprise a Dallas Semiconductor DS-5000T that has been programmed with the algorithms needed in measuring instruments 10 or 80. The DS-5000T includes 32K bits of non-volatile RAM. The standard Intel 80C51-type instruction set is used in programming the unit. Microprocessor 22 can preferably be powered down between instrument measurement periods to save power and prevent heating. It takes approximately twenty milliseconds to make an ice thickness measurement from an off-condition. Instrument 10 can therefore operate on a low duty cycle, since ice layer thicknesses do not change very rapidly in the typical application.

The measurement of antenna admittance requires a four-quadrant inverse tangent program which determines the phase of the output voltage ratio (Γ) of bridges 14 or 86. The magnitude (E) of the bridge signal is determined in a second calibration program. This data is used in a third program to compute the admittance of the antenna. If the susceptance is not sufficiently small, microprocessor 22 generates an incremental tuning signal for the frequency generator to find a frequency point of reduced antenna susceptance.

Once the resonant frequency and conductance have been determined, a frequency modulator program within microprocessor 22 causes the signal applied to the antenna to be frequency modulated with digital modulation. The operational role of the antenna is thus changed from that of a sensor to a more traditional role of a radio transmitter antenna. The modulation conveys the resonant frequency, conductance, ice thickness, surface temperature and station source identification numbers of the particular instrument. A "dithered" frequency transmission may be used to permit multiple units to be operated such that one remote receiver can receive over time all the transmitted signals without excessive interference between simultaneously transmitting instruments.

A sleep timer program within microprocessor 22 is preferably included to reduce the power duty cycle of the whole instrument 10 and/or 80. The benefit of this reduced power duty cycle can be illustrated by example. If measurements are made every minute, the resulting duty cycle can be as little as 0.0003. Estimated demand current of instrument 10, for example, is approximately 500 mA. The sleep mode current is one hundred microamperes. Therefore, the average current will be only slightly more than one hundred microamperes. It is possible, therefore, to use batteries to power instruments 10 and 80 that can be expected to last years. To further extend battery life, a surface temperature sensor may be included that controls when the transmitter is activated. For example, when temperatures approach freezing. A self-contained, unattended instrument installation is thus practical.

Figure 5:
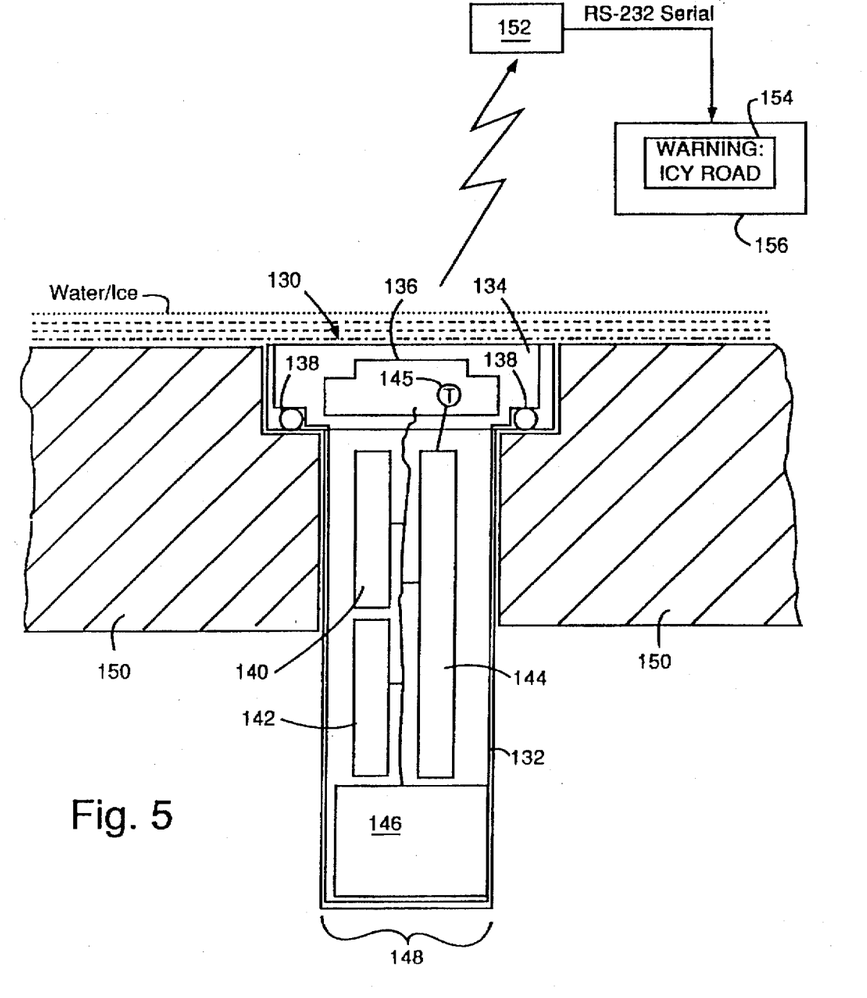
FIG. 5 is a side view of an embedded roadway sensor embodiment of the present invention positioned within a hole in a roadway shown in cross-sectional view.

FIG. 5 illustrates a roadway sensor embodiment of the present invention, referred to by the general reference numeral 130. Sensor 130 is intended to measure and interpret roadway surface accumulations including: ice presence, ice thickness, water presence, slush, snow, antifreeze mixture, roadway temperature and the freezing point. Sensor 130 comprises a two inch diameter housing 132, a ceramic cover 134, a microstrip antenna 136, an O-ring seal 138, a measurement printed circuit board (PCB) 140, a frequency synthesis and encoder 142, a microcomputer 144, a temperature sensor 145 and a lithium battery 146. All active electronic elements, such as microcomputer 144, comprise low power devices, e.g., CMOS logic. Sensor 130 fits within a hole 148 within a roadway 150. The circuit configuration of sensor 130 may comprise that of instruments 10 or 80.

Antenna 136 may include multiple mode capability, such that it exhibits two resonant frequencies $f_1$ and $f_2$. Which frequency is being used for resonance is discriminated by PCB 140.

Preferably, antenna 136 and cover 134 are comprised of materials that have thermal conductivities that match that of the surrounding structure when sensor 10 has been deployed, e.g., in FIG. 5, roadway 150. In other applications, such as in a bridge, the thermal conductivity will most likely need to be that of concrete. In airplane airfoil applications, the thermal conductivity of aluminum will typically need to be approximated. The matching of the thermal conductivity of elements of sensor 10 to the thermal conductivity of the surrounding structure is important because sensor 10 should not experience reaching a freezing temperature any sooner or later than the surrounding structure. Differences in thermal conductivity may promote or impede accurate temperate sensing and phase changes of water to ice.

Once a set of measurements by sensor 130 are complete, and a surface temperature has been read from temperature sensor 145, the roadway conditions are encoded and used to modulate a sensor-transmitter signal by encoder 142. A roadside receiver 152 receives many such signals from a plurality of sensors 130. A message 154 is then communicated by receiver 152 to a roadside warning sign 156. Microcomputer 144 includes a program to periodically "wake-up" sensor 130 and to put it back "asleep" to conserve power from battery 146. Alternatively, temperature sensor 145 may be used to control when sensor 130 wakes up, e.g., when the freezing point is being approached and an icing hazard is developing, or threatening. Battery life can thus be extended to five years or more. In order to reduce conflicts between simultaneously transmitting sensors 130, an "aloha" transmission scheme, developed and publicly disseminated by the University of Hawaii, is preferably included to schedule transmissions for random times. For a one hundred and twenty-seven sensor system, the probability of a successful transmission can approach 0.0414, and the probability of detecting at least one in three transmissions is 0.9999.

In an alternative embodiment, receiver 152 is incorporated into a vehicle, such as an automobile, truck or bus. Warning sign 156 is located within the vehicle and messages 154 are visible to a driver, and may be audibly annunciated to attract attention.

Sensor 130 may be modified physically, as is appropriate for the application, to be useful in aircraft and spacecraft. For example, a sensor 130 may be embedded in the surface of a NASA Space Shuttle Orbiter to detect and measure ice build-up on the outside surfaces of liquid oxygen fuel tanks. Receiver 152 is adapted to fit a launching pad and RS-232 cables are used to communicate conditions to display 156 which is located within a space-flight control center.

Sensor 130 may also be adapted to fit flush in the surfaces of a airplane's wings that are subject to icing and that create a hazard if icing is built-up beyond a particular critical thickness. Sensor 130 may also be adapted to measure ice build up on simulated wing surfaces located next to a runway. Sensors 130 may be positioned in runway and taxiway surfaces. Receiver 152 is adapted with RS-232 cables that communicate conditions to display 156, which is located within an airport traffic control tower. Alternatively, or in addition, the information may be communicated to the particular airplane's flight deck such that the pilots may make important decisions related to the measurements. For example, built-in de-icers in the wings may be turned on for the duration of an icing condition alert.

Figure 6:
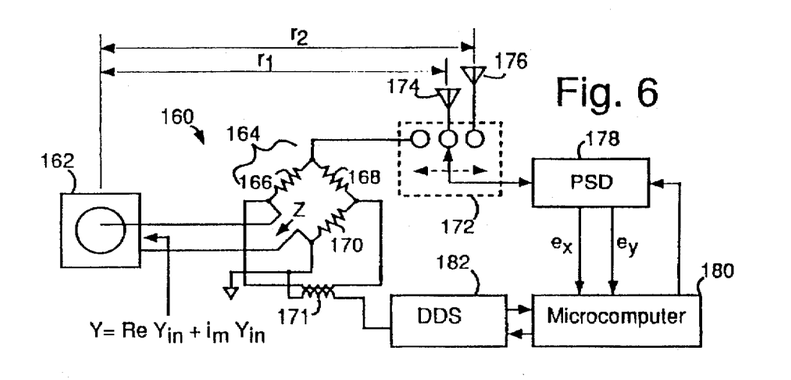
FIG. 6 is a three-antenna instrument embodiment of the present invention for measuring ice and water accumulation layers.

Instruments 10 and 80 may be modified to include an additional pair of antennas that assist in determining the thickness of accumulations of ice and water or the thickness of a layer of coal. FIG. 6 illustrates an instrument 160 comprising a circular patch antenna 162, a Maxwell bridge 164 that includes a set of three resistors 166, 168 and 170 and an injection transformer 171, a switch 172, a first receiving antenna 174 and a second receiving antenna 176, a phase sensitive detector (PSD) 178, a microcomputer 180 and a direct digital synthesizer (DDS) 182. Antennas 162, 174 and 176 are all mounted flush in a common surface subject to weather accumulations of ice, snow and/or water. Antenna 174 is mounted a radius dimension $r_1$ from antenna 162. Antenna 176 is mounted a radius dimension $r_2$ from antenna 162. Preferably, $\lambda/2\pi < r_1 < r_2$. Antennas 174 and 176 may be dipole types. The electrical parameters of the accumulation layers, e.g., conductivity ($\sigma$), permittivity ($\epsilon$), and magnetic permeability ($\mu$), can be measured with a method similar to that described by Grubb, et al., "Borehole measurements of conductivity and dielectric constant in the 300 KHz to 25 MHz frequency range," *Radio Science*, Vol. 11, no. 4, pp. 275–283, April 1976 (Published by the American Geophysical Union, Washington, D.C.). Switch 172 is temporarily positioned to connect antenna 174 to PSD 178 so that microcomputer 180 may collect the respective values $e_x$ and $e_y$. Switch 172 is then positioned to connect antenna 176 to PSD 178 so that microcomputer 180 may collect a second set of respective values $e_x$ and $e_y$. Antenna 174 produces, $$E_1 = E_o \frac{e^{-ikr_1}}{r_1}, \quad (21)$$

and antenna 176 produces, $$E_2 = E_o \frac{e^{-ikr_2}}{r_2}, \quad (22)$$

where, $$k = \beta - i\alpha, \quad (23)$$

$\beta$ is the phase constant in radians per meter, and $\alpha$ is the attenuation rate in nepers per meter, then $$-ikr_1 = -i\beta r_1 - \alpha r_1, \quad (24A)$$

$$-ikr_2 = -i\beta r_1 - \alpha r_2. \quad (24B)$$

Then, $$E_1 = \frac{E_o}{r_1} e^{-i\beta r_1} e^{-\alpha r_1}, \quad (25)$$

and, $$E_2 = \frac{E_o}{r_2} e^{-i\beta r_2} e^{-\alpha r_2}. \quad (26)$$

With $r_1$ and $r_2$ known, the attenuation or change in the magnitude, in nepers, of the signal is given by, $$\mathrm{Ln}\left|\frac{E_1}{E_2}\right| = \mathrm{Ln}\left(\frac{r_2}{r_1}\right) - (\mathrm{Ln}e^{-\alpha r_1} - \mathrm{Ln}e^{\alpha r_2}) = \quad (27)$$

$$\mathrm{Ln}\left(\frac{r_2}{r_1}\right) - \alpha(r_1 - r_2),$$

and for phase, the phase shift, in radians, is given by, $$\Delta\theta = -\beta(r_1 - r_2). \quad (28)$$

when $\Delta\theta$ is the measured phase shift. From Grubb, et al., if the magnitude and phase of signal from antennas 174 and 176 (A1 and A2) are known, then, $$\beta = \frac{\Delta\theta_r}{r_2 - r_1}, \quad (29)$$

in radian per meter, and, $$\alpha = \frac{\mathrm{Ln}\left|\frac{E_1}{E_2}\right| - \mathrm{Ln}\left|\frac{r_1}{r_2}\right|}{(r_2 - r_1)}, \quad (30)$$

in nepers per meter.

From Heaviside, where $\beta$ is the phase constant in radians per meter, $$\beta = \omega\left[\frac{\mu\epsilon}{2}\left(\left[1 + \left(\frac{\sigma}{\epsilon\omega}\right)^2\right]^{\frac{1}{2}} + 1\right)\right]^{\frac{1}{2}}, \quad (31)$$

and $\alpha$ is the attenuation rate in nepers per meter, $$\alpha = \omega\left[\frac{\mu\epsilon}{2}\left(\left[1 + \left(\frac{\sigma}{\epsilon\omega}\right)^2\right]^{\frac{1}{2}} - 1\right)\right]^{\frac{1}{2}}, \quad (32)$$

can be found $\sigma/\omega\epsilon$, the loss tangent. From this, empirically derived relationships of $\mathrm{Re}(Y_{in})$ versus thickness can be indexed or an analytical formula used to find an answer to the accumulation layer thickness and/or water-ethylene glycerol concentration.

Figure 7:
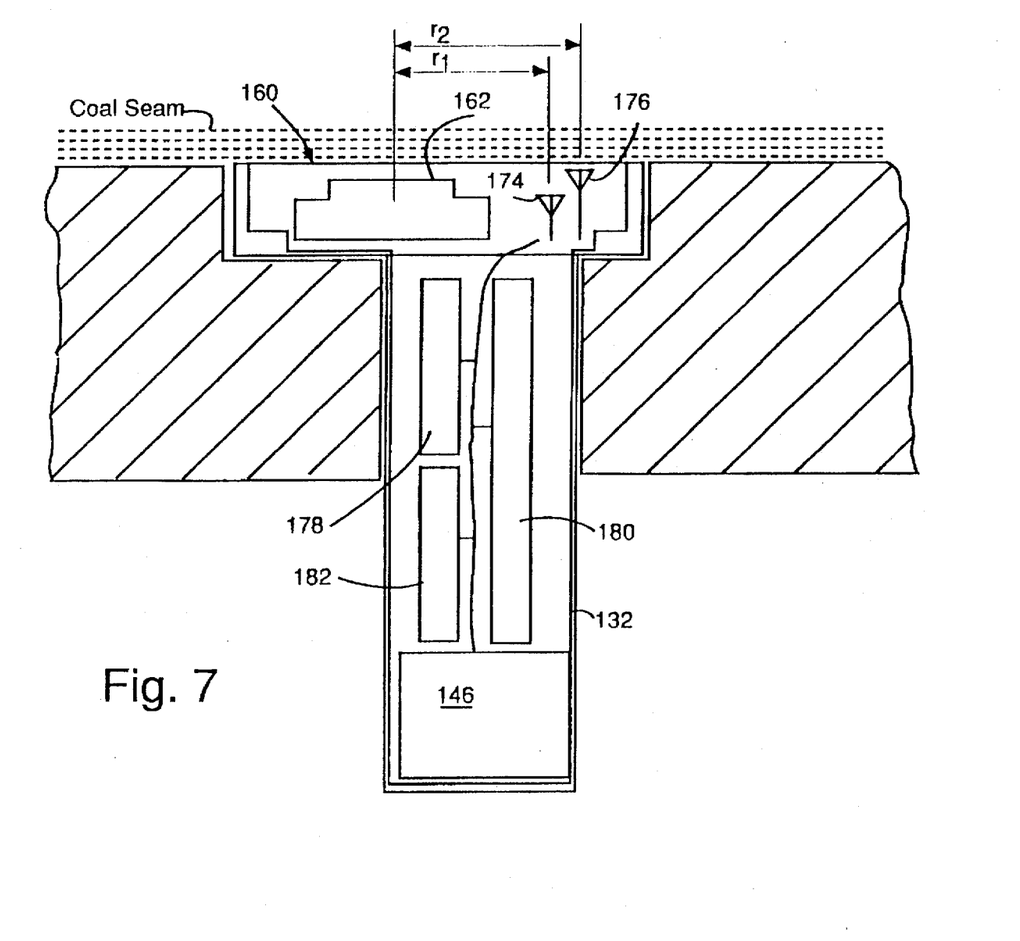
FIG. 7 is a three-antenna instrument embodiment of the present invention for measuring the thickness of coal layers or measuring a loss tangent of an antifreeze mixture layer.

FIG. 7 illustrates instrument 160 in an adaptation for sensing a coal seam. Antennas 162, 174 and 176 when placed proximate to the coal seam allow the loss tangent to be derived such that the thickness of the coal seam can be estimated even though the moisture within the coal seam may vary. This instrument configuration is used when the anti-freeze freezing-point is to be determined.

Although the present invention has been described in terms of the presently preferred embodiments, it is to be understood that the disclosure is not to be interpreted as limiting. Various alterations and modifications will no doubt become apparent to those skilled in the art after having read the above disclosure. For example, the instruments described herein may be used to measure open channel liquid flows, such as sewage passing through measuring flumes. Lard build-up, which is a common source of error in sewage flow measurement, may be discriminated out by its characteristic dielectric constant, which is substantially different than that of water. Accordingly, it is intended that the appended claims be interpreted as covering all alterations and modifications as fall within the true spirit and scope of the invention.

What is claimed is:

1. A measurement system, comprising:

an antenna for placement proximate to a surface location subject to accumulation of ice and/or water layer and that exhibits a resonant frequency and an input admittance including a real term;

Maxwell bridge means coupled to the antenna for detecting said resonant frequency, said input admittance and said real term; and frequency sweeping means for driving the antenna at a plurality of frequencies proximate in frequency to said resonant frequency wherein said resonant frequency, said input admittance and said real term may be determined.

2. The system of claim 1, further comprising:

phase sensitive detection means for determining an attenuation rate and phase and thereby a conductivity ($\sigma$) and dielectric ($\epsilon$) measurement associated with said layer; and computational means for relating said conductivity and dielectric measurements to determine ice and water content, anti-freeze freezing point and layer thickness.

3. The system of claim 2, further comprising:

communication means for conveying said measurements to a radio receiver.

4. The system of claim 3, wherein:

said receiver is adapted for inclusion in an aircraft control tower and includes graphical means for displaying ice build up conditions from an aircraft surface sensor.

5. The system of claim 3, wherein:

said receiver is adapted for inclusion in a motor vehicle and includes graphical means for displaying ice build up conditions to a driver of said motor vehicle.

6. The system of claim 3, wherein:

said receiver is adapted for locating next to a roadway and for activating a sign to alert drivers of a road hazard.

7. The system of claim 2, wherein the communication means further comprises:

frequency/phase modulating means for modulating the frequency sweeping means to apply a modulated radio transmission signal to the sensor antenna wherein the sensor antenna operates as a transmitting antenna between measurements; and coding means for translating said measurements to a modulation signal coupled to the frequency modulating means.

8. The system of claim 1, further comprising:

a battery for powering the system; and automatic power-up and power-standby means for periodically cycling the system wherein average power drain from the battery is reduced.

9. The system of claim 8, further comprising:

temperature sensing means for providing a surface temperature such that a freezing point may be determined and to control the automatic power-up and power-standby means.

10. The system of claim 1, further comprising:

temperature sensing means for determining a temperature of said surface proximate to the antenna.

11. The system of claim 7, further comprising:

a housing for the system for embedding the system flush in a roadway wherein roadway water depth and ice/slush conditions may be determined to periodically communicate any hydroplaning hazard and ice/antifreeze/water mixtures information to a radio receiver.

12. The system of claim 7, further comprising:

a housing for the system for embedding the airfoil surfaces of an airplane wing wherein icing conditions may be determined and the information periodically communicated to a radio receiver.

13. The system of claim 7, further comprising:

a battery for powering the system;

automatic power-up and power-standby means for periodically cycling the system wherein average power drain from the battery is reduced;

a housing for the system for embedding the system flush in a surface subject to weather conditions wherein water depth and ice/slush conditions may be determined to periodically communicate ice/antifreeze/water mixture information to a radio receiver.

14. The system of claim 1, wherein:

the antenna comprises materials having a thermal conductivity that approximates the thermal conductivity of a material which substantially comprises said surface location.

* * * * *